US009365476B2

(12) United States Patent
Drysdale

(10) Patent No.: US 9,365,476 B2
(45) Date of Patent: Jun. 14, 2016

(54) ARYL COMPOUNDS MODIFIED WITH PERFLUOROVINYL ETHERS

(71) Applicant: E I DU PONT DE NEMOURS AND COMPANY, Wilmington, DE (US)

(72) Inventor: Neville Everton Drysdale, Newark, DE (US)

(73) Assignee: E I DU PONT DE NEMOURS AND COMPANY, Wilmington, DE (US)

( * ) Notice: Subject to any disclaimer, the term of this patent is extended or adjusted under 35 U.S.C. 154(b) by 208 days.

(21) Appl. No.: 14/068,784

(22) Filed: Oct. 31, 2013

(65) Prior Publication Data

US 2014/0135535 A1    May 15, 2014

Related U.S. Application Data

(60) Provisional application No. 61/726,273, filed on Nov. 14, 2012.

(51) Int. Cl.
*C07C 43/315*    (2006.01)

(52) U.S. Cl.
CPC .................................... *C07C 43/315* (2013.01)

(58) Field of Classification Search
None
See application file for complete search history.

(56) References Cited

U.S. PATENT DOCUMENTS

| 4,460,791 | A  | 7/1984  | Cooke |
| 4,577,036 | A  | 3/1986  | Falk |
| 4,876,018 | A  | 10/1989 | Karydas |
| 5,198,570 | A  | 3/1993  | Feiring |
| 5,643,495 | A  | 7/1997  | Bartmann et al. |
| 5,646,222 | A  | 7/1997  | Maekawa et al. |
| 7,531,700 | B2 | 5/2009  | Petrov |
| 2006/0006364 | A1 | 1/2006  | Shundo et al. |
| 2007/0134440 | A1 | 6/2007  | Kato |
| 2011/0001088 | A1 | 1/2011  | Ootsuki et al. |
| 2012/0277460 | A1 | 11/2012 | Percec et al. |

FOREIGN PATENT DOCUMENTS

| DE | 3828063    | A1 | 2/1990  |
| DE | 4015681    | A1 | 11/1991 |
| DE | 4015681    | C2 | 11/1991 |
| EP | 0295813    | A2 | 12/1988 |
| EP | 0355025    | A2 | 8/1989  |
| EP | 0355025    | A3 | 8/1989  |
| EP | 0391390    | A1 | 10/1990 |
| EP | 0391390    | B1 | 10/1990 |
| EP | 0610861    | A1 | 8/1994  |
| EP | 0638629    | A2 | 2/1995  |
| EP | 0638629    | A3 | 2/1995  |
| EP | 0638629    | B1 | 2/1995  |
| EP | 1036790    | A1 | 9/2000  |
| EP | 1411104    | A1 | 4/2004  |
| EP | 1411104    | B1 | 5/2007  |
| GB | 1376315    | A  | 12/1974 |
| GB | 1404351    | A  | 8/1975  |
| GB | 2245587    | A  | 1/1992  |
| JP | 04159272   |    | 6/1992  |
| JP | 1994172266 | A  | 6/1994  |
| JP | 1997255608 | A  | 9/1997  |
| JP | 2006117564 | A  | 5/2006  |
| JP | 2006137856 | A  | 6/2006  |
| JP | 2011148761 | A  | 8/2011  |
| WO | 2007/149449 | A2 | 12/2007 |
| WO | 2007/149449 | A3 | 12/2007 |

OTHER PUBLICATIONS

U.S. Appl. No. 14/068,535, filed Oct. 31, 2013, Drysdale.
U.S. Appl. No. 14/068,603, filed Oct. 31, 2013, Drysdale.
U.S. Appl. No. 14/068,930, filed Oct. 31, 2013, Drysdale.
Search Report and Written Opinion, PCT/2013/069020 Dated Jan. 20, 2014.
Search Report and Written Opinion, PCT/2013/069029 Dated Jan. 7, 2014.
Search Report and Written Opinion, PCT/2013/069031 Dated Jan. 14, 2014.
Search Report and Written Opinion, PCT/2014/062643 Dated Dec. 12, 2014.
Furin, G. et al. "Reaction of 1,1,2-trifluoro-2-hexaflouro-2'-(heptafluoropropoxy-propoxyethylene with amines or alcohols", Journal of Fluorine Chemistry, 106, (2000), pp. 13-14, XP002718135, pp. 13-24.
Dlouha, Ivine, Reactivity Study of 1,1,2,4,4,5,7,7,8,8,9,9,9-tridecafluoro-5-trifluoromethyl-3,6-dioxanon-1-ene in nucleophilic reactions: fluorination properties of secondary amine adducts, Journal of Fluorine Chemistry, 117, (2002), pp. 149-159.
Non-Final Office Action Dated Sep. 30, 2014.

*Primary Examiner* — Rosalynd Keys

(57) ABSTRACT

A compound of formula (I)

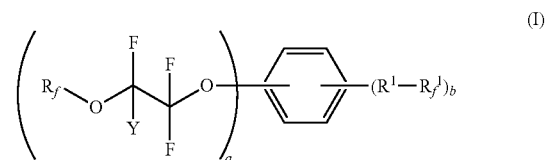

wherein
$R_f$ is $CF_3$, $-C_2F_5$, $-CF_2CFXCF_3$;
X is $-F$, or $-OC_3F_7$;
Y is $-H$, $-Cl$, or $-Br$;
$R^1$ is $-(CH_2)_q-$, $-(OCH_2CH_2)_t-$, or $-(CH_2)_q(OCH_2CH_2)_t-$;
$R_f^1$ is $-OCF_2CFY^1-O-R_f^2$;
$R_f^2$ is $-CF_3$, $-C_2F_5$, $-CF_2CFX^1CF_3$;
$X^1$ is $-F$, or $-OC_3F_7$;
$Y^1$ is $-H$, $-Cl$, or $-Br$;
q is 0 to 10;
t is 1 to 10;
a is 1 to 5; and
b is 1 to 5.

16 Claims, No Drawings

ARYL COMPOUNDS MODIFIED WITH PERFLUOROVINYL ETHERS

FIELD OF THE INVENTION

The present invention comprises aryl compounds having at least two partially fluorinated pendent groups which can be useful as additives for fluorinated oils and greases or as fluorinated solvents.

BACKGROUND OF THE INVENTION

Fluorinated oil additives are generally produced from alcohols to which are expensive and are prepared through several step synthesis. These alcohols are either then reacted to make additives or solvents. New starting materials are needed that do not utilize linear perfluorinated alcohols.

U.S. Pat. No. 7,531,700 teaches fluorinated solvents having benzene is rings with a) perfluorinated pendent alkyl groups, b) alkyl, alkoxy, or oxyalkyl groups and c) optionally halogen pendent groups useful for the manufacture of organic electronic devices. These solvents are non-reactive.

Patent Application WO 20071149449 teaches fluoroalkoxystyrenes prepared by contacting fluorinated olefin with a solution of hydroxystyrene. These fluoroalkoxystyrenes are useful in resins, elastomers, polymers, or coatings.

Compounds useful as additives for fluorinated oils and greases or as fluorinated solvents which can be prepared from starting materials other than linear perfluorinated alcohols are needed. A simpler preparation and lower cost starting materials would contribute to wider availability of such additives and solvents. The present invention meets this need.

SUMMARY OF THE INVENTION

The present invention comprises a compound of formula (I)

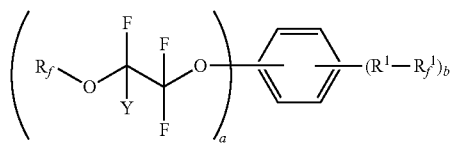

wherein
$R_f$ is —$CF_3$, —$C_2F_5$, —$CF_2CFXCF_3$;
X is —F, or —$OC_3F_7$;
Y is —H, —Cl, or —Br;
$R^1$ is —$(CH_2)_q$—, —$(OCH_2CH_2)_t$—, or —$(CH_2)_q(OCH_2CH_2)_t$—;
$R_f^1$ is —$OCF_2CFY^1$—O—$R_f^2$;
$R_f^2$ is —$CF_3$, —$C_2F_5$, —$CF_2CFX^1CF_3$;
$X^1$ is —F, or —$OC_3F_7$;
$Y^1$ is —H, —Cl, or —Br;
q is 0 to 10;
t is 1 to 10;
a is 1 to 5; and
b is 1 to 5.

DETAILED DESCRIPTION

Herein trademarks are shown in upper case.
The term "(meth)acrylate" is used herein defined to mean both "acrylate" and "methacrylate".

The present invention provides a compound of formula (I)

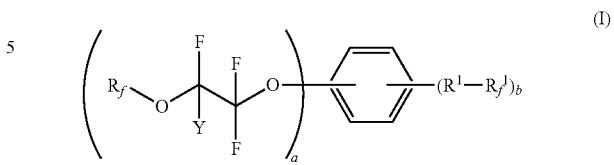

wherein
$R_f$ is —$CF_3$, —$C_2F_5$, —$CF_2CFXCF_3$;
X is —F, or —$OC_3F_7$;
Y is —H, —Cl, or —Br;
$R^1$ is —$(CH_2)_q$—, —$(OCH_2CH_2)_t$—, or —$(CH_2)_q(OCH_2CH_2)_t$—;
$R_f^1$ is —$OCF_2CFY^1$—O—$R_f^2$;
$R_f^2$ is —$CF_3$, —$C_2F_5$, —$CF_2CFX^1CF_3$;
$X^1$ is —F, or —$OC_3F_7$;
$Y^1$ is —H, —Cl, or —Br;
q is 0 to 10;
t is 1 to 10;
a is 1 to 5; and
b is 1 to 5.

Compounds of the present invention include pendent groups $(R_f$—O—$CFY$—$CF_2O$—$)_a$ and $(—R^1—R_f^1)_b$ and wherein a is 1 to 5 and b is 1 to 5. Compounds of the present invention may have 1, 2, 3, 4, or 5 pendent groups of $R_f$—O—$CFY$—$CF_2O$—; 1, 2, 3, 4, or 5 pendent groups of —$R^1$—$R_f^1$; and mixtures thereof; provided that the total number of pendent groups is less than or equal to 6. The $R_f$—O—$CFY$—$CF_2O$— and —$R^1$—$R_f^1$ groups may be ortho, para, or meta on the benzene ring or combinations thereof.

Preferred compounds of Formula (I) include those wherein $R_f$ is —$CF_3$, or —$C_2F_5$; Y is H; $R^1$ is —$(CH_2)_q$—, —$(OCH_2CH_2)_t$—, or —$(CH_2)_q(OCH_2CH_2)_t$—; $R_f^1$ is —$OCF_2CFY^1$—O—$R_f^2$; $R_f^2$ is —$CF_3$ or —$C_2F_5$; $Y^1$ is —H; a and b are defined as above; q is 1, 2, 3, 4, 5, or 6; and t is 1, 2, 3, 4, 5, or 6. Also preferred are compounds of Formula (I) wherein $R_f$ is —$CF_3$, or —$C_2F_5$; Y is H; $R^1$ is —$(CH_2)_q$—, —$(OCH_2CH_2)_t$—, or —$(CH_2)_q(OCH_2CH_2)_t$—; $R_f^1$ is —$OCF_2CFY^1$—O—$R_f^2$; $R_f^2$ is —$CF_3$ or —$O_2F_5$; $Y^1$ is —H; a and b are defined as above; q is 1, 2, or 3; and t is 1, 2, or 3.

Preferred compounds of Formula (I) also include those wherein $R_f$ is —$CF_3$, or —$C_2F_5$; Y is H; $R^1$ is —$(CH_2)_q$—, —$(OCH_2CH_2)_t$—, or —$(CH_2)_q(OCH_2CH_2)_t$—; $R_f^1$ is —$OCF_2CFY^1$—O—$R_f^2$; $R_f^2$ is —$CF_2CFX^1CF_3$; $X^1$ is —F, or —$OC_3F_7$; $Y^1$ is —H; a and b are defined as above; q is 1, 2, 3, 4, 5, or 6; and t is 1, 2, 3, 4, 5, or 6. Also preferred are compounds of Formula (I) wherein $R_f$ is —$CF_3$, or —$C_2F_5$; Y is H; $R^1$ is —$(CH_2)_q$—, —$(OCH_2CH_2)_t$—, or —$(OH_2)_q(OCH_2CH_2)_t$—; $R_f^1$ is —$OCF_2CFY^1$—O—$R_f^2$; $R_f^2$ is —$CF_2CFX^1CF_3$; $X^1$ is —F, or —$OC_3F_7$; $Y^1$ is —H; a and b are defined as above; q is 1, 2, or 3; and t is 1, 2, or 3.

Preferred compounds of Formula (I) also include those wherein $R_f$ is —$CF_2CFXCF_3$; X is —F, or —$OC_3F_7$; Y is H; $R^1$ is —$(CH_2)_q$—, —$(OCH_2CH_2)_t$—, or —$(OH_2)_q(OCH_2CH_2)_t$—; $R_f^1$ is —$OCF_2CFY^1$—O—$R_f^2$; $R_f^2$ is —$CF_2CFX^1CF_3$; $X^1$ is —F, or —$OC_3F_7$; $Y^1$ is —H; a and b are defined as above; q is 1, 2, 3, 4, 5, or 6; and t is 1, 2, 3, 4, 5, or 6. Also preferred are compounds of Formula (I) wherein $R_f$ is —$CF_2CFXCF_3$; X is —F, or —$OC_3F_7$; Y is H; $R^1$ is —$(CH_2)_q$—, —$(OCH_2CH_2)_t$—, or —$(CH_2)_q(OCH_2CH_2)_t$—; $R_f^1$ is —$OCF_2CFY_1$—O—$R_f^2$; $R_f^2$ is —$CF_2CFX^1CF_3$; $X^1$ is —F, or —$OC_3F_7$; $Y^1$ is —H; a and b are defined as above; q is 1, 2, or 3; and t is 1, 2, or 3.

Additional preferred compounds of Formula (I) include those wherein $R_f$ is —$CF_3$, —$C_2F_5$, or —$CF_2CFXCF_3$; X is —F, or —$OC_3F_7$; Y is H; $R^1$ is —$(CH_2)_q$—; $R_f^1$ is —$OCF_2CFY^1$—O—$R_f^2$; $R_f^2$ is —$CF_3$, —$C_2F_5$, —$CF_2CFX^1CF_3$; $X^1$ is —F, or —$OC_3F_7$; $Y^1$ is —H; a, and b are defined as above; and q is 1, 2, 3, 4, 5, or 6. Also preferred are compounds of Formula (I) wherein $R_f$ is —$CF_3$, —$C_2F_5$, or —$CF_2CFXCF_3$; X is —F, or —$OC_3F_7$; Y is H; $R^1$ is —$(CH_2)_q$—; $R_f^1$ is —$OCF_2CFY^1$—O—$R_f^2$; $R_f^2$ is —$CF_3$, —$C_2F_5$, —$CF_2CFX^1CF_3$; $X^1$ is —F, or —$OC_3F_7$; $Y^1$ is —H; a, and b are defined as above; and q is 1, 2, or 3.

Additional preferred compounds of Formula (I) include those wherein $R_f$ is —$CF_3$, —$C_2F_5$, or —$CF_2CFXCF_3$; X is —F, or —$OC_3F_7$; Y is H; $R^1$ is —$(OCH_2CH_2)_t$—; $R_f^1$ is —$OCF_2CFY^1$—O—$R_f^2$; $R_f^2$ is —$CF_3$, —$C_2F_5$, or —$CF_2CFX^1CF_3$; $X^1$ is —F, or —$OC_3F_7$; $Y^1$ is —H; a, and b are defined as above; and t is 1, 2, 3, 4, 5, or 6. Also preferred are compounds of Formula (I) wherein $R_f$ is —$CF_3$, —$C_2F_5$, or —$CF_2CFXCF_3$; X is —F, or —$OC_3F_7$; Y is H; $R^1$ is —$(OCH_2CH_2)_t$—; $R_f^1$ is —$OCF_2CFY^1$—O—$R_f^2$; $R_f^2$ is —$CF_3$, —$O_2F_5$, or —$CF_2CFX^1CF_3$; $X^1$ is —F, or —$OC_3F_7$; $Y^1$ is —H; a, and b are defined as above; and t is 1, 2, or 3.

Additional preferred compounds of Formula (I) include those wherein $R_f$ is —$CF_3$, —$C_2F_5$, or —$CF_2CFXCF_3$; X is —F, or —$OC_3F_7$; Y is H; $R^1$ is —$(CH_2)_q(OCH_2CH_2)_t$—; $R_f^1$ is —$OCF_2CFY^1$—O—$R_f^2$; $R_f^2$ is —$CF_3$, —$C_2F_5$, or —$CF_2CFX^1CF_3$; $X^1$ is —F, or —$OC_3F_7$; $Y^1$ is —H; a, and b are defined as above; q is 1, 2, 3, 4, 5, or 6; and t is 1, 2, 3, 4, 5, or 6. Also preferred are compounds of Formula (I) wherein $R_f$ is —$CF_3$, —$C_2F_5$, or —$CF_2CFXCF_3$; X is —F, or —$OC_3F_7$; Y is H; $R^1$ is —$(CH_2)_q(OCH_2CH_2)_t$—; $R_f^1$ is —$OCF_2CFY^1$—O—$R_f^2$; $R_f^2$ is —$CF_3$, —$C_2F_5$, or —$CF_2CFX^1CF_3$; $X^1$ is —F, or —$OC_3F_7$; $Y^1$ is —H; a, and b are defined as above; q is 1, 2, or 3; and t is 1, 2, or 3.

Compounds of Formula (I) can be produced in various ways. Examples of compounds of Formula (I) include, but not limited to,

(II)

wherein $R^1$ is —$(CH_2)_q$—, —$(OCH_2CH_2)_t$—, or —$(CH_2)_q(OCH_2CH_2)_t$—.

In the present invention, compounds of the present invention of Formula (I), wherein $R_f$ is —$CF_3$, —$C_2F_5$, —$CF_2CFXCF_3$; X is —F, or —$OC_3F_7$; Y is —H, —Cl, or —Br and $R^1$ is —$(CH_2)_q$—, —$(OCH_2CH_2)_t$—, or —$(CH_2)_q(OCH_2CH_2)_t$—; $R_f^1$ is —$OCF_2CFY^1$—O—$R_f^2$; $R_f^2$ is —$CF_3$, —$C_2F_5$, —$CF_2CFX^1CF_3$; $X^1$ is —F, or —$OC_3F_7$; $Y^1$ is —H, —Cl, or —Br can be prepared by contacting compounds of Formula (III)

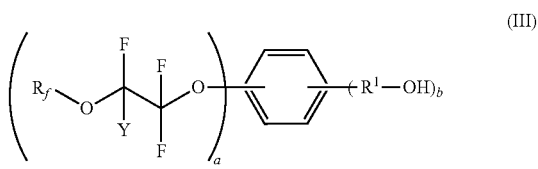
(III)

wherein $R^1$ is —$(CH_2)_q$—, —$(OCH_2CH_2)_t$—, or $(CH_2)_q(OCH_2CH_2)_t$— with one or more of a second perfluorovinyl ether of formula (IV)

(IV)

wherein $R_f^1$ is —$OCF_2CFY^1$—O—$R_f^2$; wherein $R_f^2$ is —$CF_3$, —$C_2F_5$, —$CF_2CFX^1CF_3$; $X^1$ is —F, or —$OC_3F_7$; $Y^1$ is —H, —Cl, or —Br in a solvent and a base. Suitable bases include those known to deprotonate the hydrogen of a phenol. Examples of such bases include, but are not limited to, potassium carbonate, sodium carbonate, and potassium bicarbonate. Examples of such bases include, but are not limited to, potassium carbonate, sodium carbonate, and potassium bicarbonate. Examples of suitable solvents include, but are not limited to, tetrahydrofuran, carbon tetrachloride, and carbon tetrabromide. In Formula (I), when tetrahydrofuran is the solvent, then $Y^1$ is —H. In Formula (I), when carbon tetrachloride is the solvent, then $Y^1$ is —Cl. In Formula (I), when carbon tetrabromide is the solvent, then $Y^1$ is —Br. The reaction temperature can be between room temperature and the solvent reflux temperature.

For compounds of Formula (IV), when $R_f^2$ is —$CF_3$, the compound is perfluoromethylvinyl ether of Formula (V)

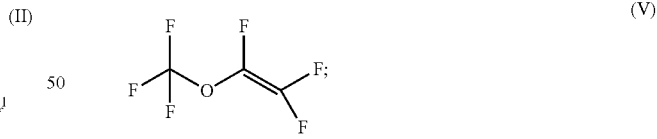
(V)

when $R_f^2$ is —$C_2F_5$, the compound is a perfluorovinyl ethyl ether of Formula (VI)

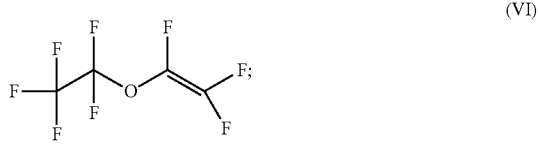 [SMILES: FC(F)=C(F)OC(F)(F)C(F)(F)F]
(VI)

when $R_f^2$ is —$CF_2CFX^1CF_3$ and $X^1$ is —F, the compound is a perfluoropropylvinyl ether of Formula (VII)

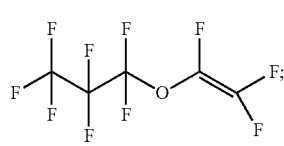

and when $R_f^2$ is —$CF_2CFX^1CF_3$ and $X^1$ is —$OC_3F_7$, the compound is a perfluoropropylvinyl ether of Formula (VIII)

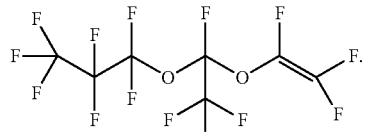

Compounds of Formula (III)

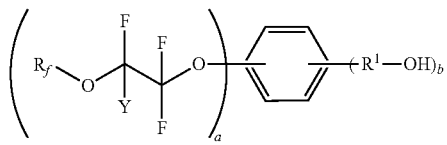

can be prepared by contacting compounds of Formula (IX)

with a first perfluorovinyl ether of Formula (X)

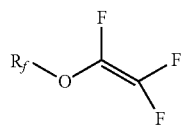

wherein $R_f$ is —$CF_3$, —$C_2F_5$, $CF_2CFXCF_3$; X is —F, or —$OC_3F_7$; and Y is —H, —Cl, or Br.

For compounds of Formula (X), when $R_f$ is —$CF_3$, the compound is perfluoromethylvinyl ether of Formula (XI)

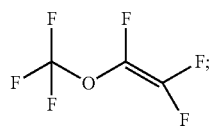

when $R_f$ is —$C_2F_5$, the compound is a perfluorovinyl ethyl ether of Formula (XII)

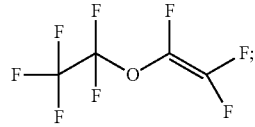

when $R_f$ is —$CF_2CFXCF_3$ and X is —F, the compound is a perfluoropropylvinyl ether of Formula (XIII)

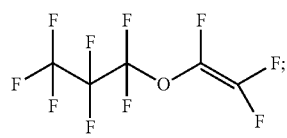

and when $R_f$ is —$CF_2CFXCF_3$ and X—$OC_3F_7$, the compound is a to perfluoropropylvinyl ether of Formula (XIV)

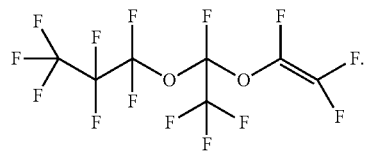

In the present invention, $R_f$ and $R_f^1$ can be the same or different, X and $X^1$ may be the same or different, and Y and $Y^1$ can be the same or different. In the case were the $R_f$ and $R_f^1$ and X and $X^1$ are be the same, the first perfluorovinyl ether of Formula (IV) and the second perfluorovinyl ether of Formula (X) are the same.

Compounds of the present invention and above defined embodiments are useful, for example, as additives for fluorinated lubricants and as fluorinated solvents.

EXAMPLES

Materials

Perfluorovinyl ethers 1,1,1,2,2,3,3-heptafluoro-3-((1,2,2-trifluorovinyl)oxy)propane and 1,1,1,2,2,3,3-heptafluoro-3-(1,1,1,2,3,3-hexafluoro-3-(1,2,2trifluorovinyl)oxy)propan-2-yloxy)propane are commercially, available from E. I. du Pont de Nemours and Company, Wilmington, Del. All other reactants, unless otherwise specified, are available from Sigma-Aldrich, St. Louis, Mo.

Example 1

1-(1,1,2-trifluoro-2-(1,1,2,3,3,3-hexafluoro-2-(perfluoropropoxy)propoxy)ethoxy)-4-((1,1,2-trifluoro-2-(1,1,2,3,3-hexafluoro-2-(perfluoropropoxy)propoxy)ethoxy)methyl)benzene In a dry box, tetrahydrofuran (50 mL) and 4-(hydroxymethyl)phenol (0.62 g, 0.005 mol) were added to a round bottom flask equipped with a stirrer. Potassium carbonate (0.345 g, 0.0025 mol) was then added to the flask. 1,1,1,2,2,3,3-Heptafluoro-3-(1,1,1,2,3,3-hexafluoro-3-(1,2,2trifluorovinyloxy)propan-2-yloxy)propane (3.24 g, 0.0075 mol) was then added via the addition funnel and the reaction was placed in an oil bath and heated to a gentle reflux over 2 days. The content was analyzed by proton NMR and shown to be (4-(1,1,2-trifluoro-2-(1,1,2,3,3,3-hexafluoro-2-(perfluoropropoxy)propoxy)ethoxy)phenyl)methanol.

In the dry box, tetrahydrofuran (10 mL) and 4-(hydroxymethyl)phenol (2.5 g, 0.0201 mol) were added to a round bottom flask equipped with a stirrer. Potassium carbonate (1.38 g, 0.01 mol) was then added to the flask. 1,1,1,2,2,3,3-Heptafluoro-3-(1,1,1,2,3,3-hexafluoro-3-(1,2,2trifluorovinyloxy)propan-2-yloxy)propane (326.1 g, 0.065 mol) was then added via the addition funnel and the reaction was placed in an oil bath and heated to a gentle reflux overnight. The content was analyzed to by proton NMR and shown to be 1-(1,1,2-trifluoro-2-(1,1,2,3,3,3-hexafluoro-2-(perfluoropropoxy)propoxy)ethoxy)-4-((1,1,2-trifluoro-2-(1,1,2,3,3,3-hexafluoro-2-(perfluoropropoxy)propoxy)ethoxy)methyl)benzene.

What is claimed is:

1. A compound of formula (I)

$$\left( R_f - O - \underset{Y}{\overset{F}{\underset{|}{C}}} - \underset{F}{\overset{F}{\underset{|}{C}}} - O \right)_a \hspace{-2pt} \begin{array}{c} \\ \end{array} \hspace{-2pt} (R^1 - R_f^1)_b$$

(I)

wherein
$R_f$ is —$CF_3$, —$C_2F_5$, —$CF_2CFXCF_3$;
X is —F, or —$OC_3F_7$;
Y is —H, —Cl, or —Br;
$R^1$ is —$(CH_2)_q$—, —$(OCH_2CH_2)_t$—, or —$(CH_2)_q(OCH_2CH_2)_t$—;
$R_f^1$ is —$OCF_2CFY^1$—O—$R_f^2$;
$R_f^2$ is —$CF_2CFX^1CF_3$;
$X^1$ is —$OC_3F_7$;
$Y^1$ is —H, —Cl, or —Br;
q is 1;
t is 1 to 10;
a is 1 to 5; and
b is 2 to 5.

2. A compound of claim 1, wherein $R_f$ is —$CF_3$.
3. A compound of claim 1, wherein $R_f$ is —$C_2F_5$.
4. A compound of claim 1, wherein $R_f$ is —$CF_2CFXCF_3$ and X is —F.
5. A compound of claim 1, wherein $R_f$ is —$CF_2CFXCF_3$ and X is —$OC_3F_7$.
6. A compound of claim 1, where $R^1$ is —$(CH_2)_q$— and q is 1.
7. A compound of claim 1, where $R^1$ is —$(OCH_2CH_2)_t$ and t is 1 to 10.
8. A compound of claim 1, where $R^1$ is —$(CH_2)_q(OCH_2CH_2)_t$— and q is 1 to 10 and t is 1 to 10.
9. A compound of claim 1, wherein Y is H.
10. A compound of claim 1, wherein Y is Cl.
11. A compound of claim 1, wherein Y is Br.
12. A compound of claim 1, wherein $Y^1$ is H.
13. A compound of claim 1, wherein $Y^1$ is Cl.
14. A compound of claim 1, wherein $Y^1$ is Br.
15. A compound of claim 1, where $R_f$ and $R_f^2$ are the same.
16. A compound of claim 1, where Y and $Y^1$ are the same.

* * * * *